United States Patent
Matlock et al.

(10) Patent No.: US 8,146,598 B2
(45) Date of Patent: *Apr. 3, 2012

(54) MEDICAL DEVICE TUBE HAVING A FLANGE WITH OPPOSING SUPPORT EARS FOR IMPROVED ALIGNMENT AND RETENTION OF AN INNER CANNULA IN AN OUTER CANNULA

(75) Inventors: George Matlock, Pleasanton, CA (US); Donald L. Moore, Livermore, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 131 days.

This patent is subject to a terminal disclaimer.

(21) Appl. No.: 12/631,015

(22) Filed: Dec. 4, 2009

(65) Prior Publication Data

US 2010/0078031 A1    Apr. 1, 2010

Related U.S. Application Data

(63) Continuation of application No. 11/237,168, filed on Sep. 28, 2005, now Pat. No. 7,647,929.

(51) Int. Cl.
*A61M 11/00* (2006.01)
(52) U.S. Cl. .............. 128/207.15; 128/200.26
(58) Field of Classification Search ............ 128/200.26, 128/207.14–207.17, 911, 912, DIG. 26
See application file for complete search history.

(56) References Cited

U.S. PATENT DOCUMENTS

| | | |
|---|---|---|
| 3,169,529 A | 2/1965 | Koenig |
| 3,225,767 A | 12/1965 | Smith |
| 3,948,273 A | 4/1976 | Sanders |
| 4,315,505 A | 2/1982 | Crandall et al. |
| 4,909,248 A | 3/1990 | McLennan |
| 5,056,515 A * | 10/1991 | Abel .................. 128/207.15 |
| 5,222,487 A | 6/1993 | Carr et al. |
| 5,390,669 A | 2/1995 | Michael et al. |
| 5,419,314 A * | 5/1995 | Christopher ......... 128/200.26 |
| 5,568,946 A * | 10/1996 | Jackowski .............. 285/38 |
| 5,996,582 A | 12/1999 | Turnbull |
| 6,102,041 A | 8/2000 | Bosignac et al. |
| 6,588,428 B2 | 7/2003 | Shikani et al. |

(Continued)

FOREIGN PATENT DOCUMENTS

EP    2086619    8/2009

(Continued)

OTHER PUBLICATIONS

Bjorling, Gunilla et al., Clinical use and Material Wear of Polymeric Tracheostomy Tubes; The American Laryngological, Rhinological and Otological Society, Inc., 2007, pp. 1552-1559, No. 117.

(Continued)

*Primary Examiner* — Steven Douglas
(74) *Attorney, Agent, or Firm* — Fletcher Yoder (57) ABSTRACT

A medical device tube having opposing support ears for improved coupling of an inner cannula to an outer cannula. The medical device tube comprises an outer cannula having opposing support ears on an outer cannula connector flange attached to a proximal end of the outer cannula. The opposing support ears maintain locking ears of the inner cannula in substantially one position. The opposing support ears substantially prevent the locking ears in contact with the outer cannula connector flange from slipping therefrom by, e.g., rotation, axial displacement, torsional shear, etc.

20 Claims, 14 Drawing Sheets

U.S. PATENT DOCUMENTS

| | | | |
|---|---|---|---|
| 6,722,369 B1 | 4/2004 | Kron | |
| 6,725,862 B2 | 4/2004 | Klinberg et al. | |
| 6,739,339 B2 | 5/2004 | Bergamaschi | |
| 6,767,355 B2 | 7/2004 | Frova et al. | |
| 6,772,758 B2 | 8/2004 | Lambert | |
| 6,796,309 B2 | 9/2004 | Nash et al. | |
| 6,840,242 B1 | 1/2005 | McCoy | |
| 6,994,088 B2 | 2/2006 | Briggs, III et al. | |
| 7,036,510 B2 | 5/2006 | Zgoda et al. | |
| 7,086,402 B2 | 8/2006 | Peterson | |
| 7,156,090 B2 | 1/2007 | Nomori | |
| 7,267,124 B1 | 9/2007 | Roberson, Jr. et al. | |
| 7,305,989 B2 | 12/2007 | Gostelow | |
| 7,308,896 B2 | 12/2007 | Cruz | |
| 7,328,702 B2 | 2/2008 | Gostelow | |
| 7,448,387 B2 | 11/2008 | Janatpour | |
| D585,980 S | 2/2009 | Cabrera | |
| 7,647,929 B2 * | 1/2010 | Matlock et al. | 128/207.15 |
| 2004/0087991 A1 | 5/2004 | Woo | |
| 2004/0098013 A1 | 5/2004 | Ciaglia et al. | |
| 2004/0177851 A1 | 9/2004 | Acosta | |
| 2004/0255954 A1 | 12/2004 | Zgoda et al. | |
| 2005/0005941 A1 | 1/2005 | Bischoff et al. | |
| 2005/0066816 A1 | 3/2005 | Wright | |
| 2005/0081860 A1 | 4/2005 | Gonzales | |
| 2005/0144761 A1 | 7/2005 | Hatcher | |
| 2005/0161047 A1 | 7/2005 | Briggs, III et al. | |
| 2005/0166924 A1 | 8/2005 | Thomas et al. | |
| 2005/0188993 A1 | 9/2005 | Steeves et al. | |
| 2005/0241643 A1 | 11/2005 | Webber | |
| 2005/0255953 A1 | 11/2005 | Puckett | |
| 2005/0259724 A1 | 11/2005 | Bergstrom et al. | |
| 2006/0060201 A1 | 3/2006 | Beagle et al. | |
| 2006/0070628 A1 | 4/2006 | Byatt et al. | |
| 2006/0081254 A1 | 4/2006 | Gostelow | |
| 2006/0124134 A1 | 6/2006 | Wood | |
| 2007/0083262 A1 | 4/2007 | Matlock | |
| 2007/0246051 A1 | 10/2007 | Newman | |
| 2007/0255258 A1 | 11/2007 | Matlock et al. | |
| 2008/0029088 A1 | 2/2008 | Freitag | |
| 2008/0072911 A1 | 3/2008 | Flagler et al. | |
| 2008/0142001 A1 | 6/2008 | Wright | |
| 2008/0142005 A1 | 6/2008 | Schnell | |
| 2008/0168986 A1 | 7/2008 | Mythen | |
| 2008/0257353 A1 | 10/2008 | Yamamoto et al. | |
| 2009/0025717 A1 | 1/2009 | Pinel | |
| 2009/0025730 A1 | 1/2009 | Pinel | |

FOREIGN PATENT DOCUMENTS

| | | |
|---|---|---|
| WO | 95/33506 | 12/1995 |
| WO | 2008046418 | 8/2009 |

OTHER PUBLICATIONS

Fricke, Bradley L. MD et al., Upper Airway Volume Segmentation Analysis using Cine MRI Findings in Children with Tracheostomy Tubes, Korean Journal of Radiology, Dec. 2007, pp. 506-511, vol. 8, Issue 6.

Saussez, S. et al., Acromegaly Presented as a Cause of Laryngeal Dyspnea, Auris Nasus Larynx International Journal of ORL and HNS, 2007, pp. 541-543, No. 34.

Liu, Y-H et al., Extra-Long Montgomery T Tube in Major Airway Stenosis, The Journal of Laryngology and Otology, 2009, pp. 772-777. No. 123.

Silicone Air Cuff Tracheostomy Tubes, Pediatric & Neonatal TT, Adjustable Neck Flange TT, Arcadia Medical, http://www.arcadiamedical.com/arcadia/main.asp?cid=4&pid=4, 2010, pp. 1-2.

Silicone Cuffless Adult Tracheostomy Tubes, Arcadia Medical, http://www.arcadiamedical.com/arcadia/main.asp?cid=4&pid=4, 2010, pp. 1-2.

Silicone Cuffless and Silicon Cuffless Extended Connect Pediatric & Neonatal Tracheostomy Tubes, Arcadia Medical, http://www.arcadiamedical.com/arcadia/main.asp?cid=4&pid=4, 2010, pp. 1-2.

Bivona Aire-Cuf Neonatal and Pediatric Tracheostomy Tubes, http://www.smiths-medical.com/catalog/bivona-tracheostomy-tubes/neo-natal-pediatric/neo-aire-cuf-neonatal.html, 2010, pp. 1-13.

Bivona Adult Mid-Range Aire-Cuf Adjustable Neck Flange Hyperflex, http://www.smiths-medical.com/catalog/bivona-tracheostomy-tubes/adult/aire-cuf/bivona-mid-range-aire-2.html, 2010, pp. 1-13.

Portex Blue Line cuffed Tracheostomy Tubes, http://www.smiths-medical.com/catalog/portex-tracheostomy-tubes/adult/blue-line-cuffed/blue-line-cuffed-tracheostmy.html, 2010, pp. 1-13.

Rusch Adjustable Flange Pediatric, http://www.teleflexmedical.com/prod_rusch.php, 2010, pp. 1-8.

Rusch QuickTrach, http://www.teleflexmedical.com/prod_rusch.php, 2010, pp. 1-5.

Rusch Trach Cap & Conn. Set, http://www.teleflexmedical.com/prod_rusch.php, 2010, pp. 1-5.

Rusch Trach Collar, http://www.teleflexmedical.com/prod_rusch.php, 2010, pp. 1-7.

Rusch Disposable Inner Cannula, http://www.teleflexmedical.com/prod_rusch.php, 2010, pp. 1-5.

Rusch PercuQuick Trach Set, http://www.teleflexmedical.com/prod_rusch.php, 2010, pp. 1-5.

Rusch Crystal, http://www.teleflexmedical.com/prod_rusch.php, 2010, pp. 1-14.

Rusch Tracheoflex, http://www.teleflexmedical.com/prod_rusch.php, 2010, pp. 1-9.

Tracoe Medical GmbH-Comfort, http://tracoe.com/products/6/comfort.html. 2010, pp. 1-4.

Tracoe Medical GmbH-mini, http://tracoe.com/products/5/mini.html. 2010, pp. 1-2.

Tracoe Medical GmbH-Percutan, http://tracoe.com/products.html. 2010, pp. 1-4.

Tracoe Medical GmbH-pure, http://tracoe.com/products/2/pure.html. 2010, pp. 1-4.

Tracoe Medical GmbH-twist, http://tracoe.com/products/4/twist.html. 2010, pp. 1-4.

Tracoe Medical GmbH-vario, http://tracoe.com/products/3/vario.html. 2010, pp. 1-4.

Device that Enables Fast, Precise Creation of Tracheal Window, University of Florida, Office of Technology Licensing, p. 1.

* cited by examiner

MEDICAL DEVICE TUBE HAVING A FLANGE WITH OPPOSING SUPPORT EARS FOR IMPROVED ALIGNMENT AND RETENTION OF AN INNER CANNULA IN AN OUTER CANNULA

CROSS REFERENCE TO RELATED APPLICATIONS

This application is a continuation of U.S. patent application Ser. No. 11/237,168, filed on Sep. 28, 2005, which is incorporated herein by reference in its entirety for all purposes.

TECHNICAL FIELD

The present disclosure, according to one embodiment, relates to medical device tubes, e.g., tracheostomy tubes, used in medical applications, and more particularly, to more securely attaching an inner cannula to an outer cannula.

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A medical device tube may include an outer cannula (slender tube that may be inserted into a body cavity) attached to a head base connector. The head base connector and outer cannula are adapted for insertion of a disposable inner cannula. One example of a medical device tube is a tracheostomy tube. The tracheostomy tube may have a curved "L" shape and the head base connector may be attached to a swivel neck plate/flange. The tracheostomy tube provides an artificial airway for access to the patient's airway for airway management. The tracheostomy tube is introduced into a tracheotomy incision in the patient's neck that provides access to the trachea. The tracheostomy tube may be secured by a swivel neck plate/flange that may be connected to a tracheostomy tube holder or neck strap, thus securing this artificial airway for spontaneous or mechanical ventilation of the patient.

The inner cannula may be inserted into the head base connector and outer cannula after the tracheostomy tube has been placed into the patient's trachea. This inner cannula typically includes a connector for quick removal of the inner cannula from the outer cannula, e.g., the inner cannula connector removably attaches to the head base connector, so that the inner cannula may be removed quickly if an obstruction, e.g., plug of mucus, sputum, etc., is formed. For example, a snap connector may be used to attached the inner cannula to the outer cannula. A mechanical ventilator hose may be removably coupled to the inner cannula to assist the patient in breathing. However, if the inner cannula is twisted and/or put into radial torsion during use, e.g., caused by movement of the ventilator hose connected thereto, the snap connector may disengage and allow the inner cannula to withdraw from the outer cannula.

SUMMARY

Improving the reliability of attachment and continued attachment retention of the inner cannula to the outer cannula may be desired. Also, an added benefit would be to do so without having to change existing designs for the inner cannula and connector.

According to a specific example embodiment of this disclosure, a medical device tube includes an outer cannula connector having a locking flange and opposing support ears; an outer cannula coupled to the outer cannula connector; an inner cannula connector having locking ears; and an inner cannula coupled to the inner cannula connector; wherein the inner cannula is adapted for insertion into the outer cannula connector and outer cannula such that the locking ears hold onto the locking flange of the outer cannula connector, wherein the opposing support ears substantially prevent rotation of the inner cannula connector in the outer cannula connector.

According to another specific example embodiment of this disclosure, a tracheostomy air passage system has a tracheostomy tube including an outer cannula connector having a locking flange and opposing support ears, an outer cannula coupled to the outer cannula connector, an inner cannula connector having locking ears, and an inner cannula coupled to the inner cannula connector, wherein the inner cannula is adapted for insertion into the outer cannula connector and outer cannula such that the locking ears hold onto the locking flange of the outer cannula connector, wherein the opposing support ears substantially prevent rotation of the inner cannula connector in the outer cannula connector; a ventilator hose coupled to the inner cannula connector; and a ventilator coupled to the ventilator hose.

BRIEF DESCRIPTION OF THE DRAWINGS

A more complete understanding of the present disclosure may be acquired by referring to the following description taken in conjunction with the accompanying drawings wherein.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION OF SPECIFIC EMBODIMENTS

Referring now to the drawings, the details of specific example embodiments are schematically illustrated. Like elements in the drawings will be represented by like numbers, and similar elements will be represented by like numbers with a different lower case letter suffix.

Figure 1:
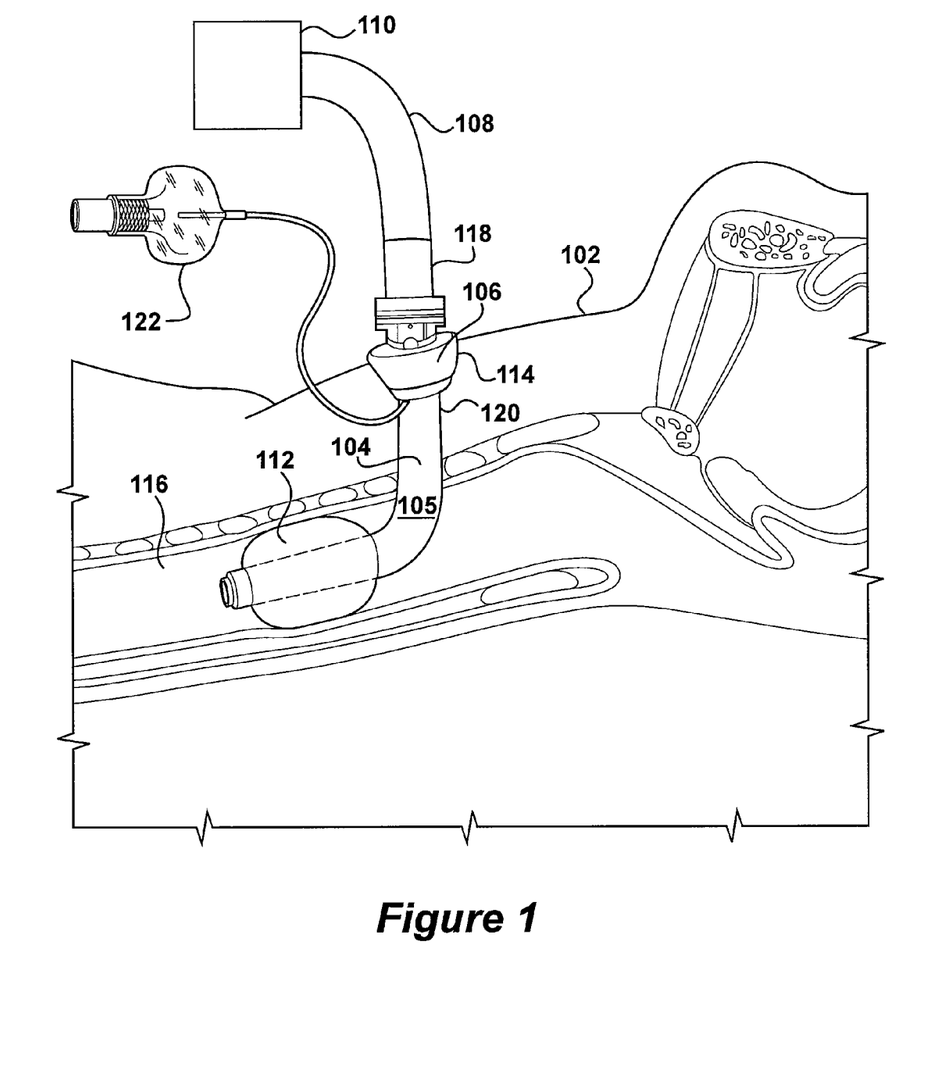
FIG. 1 illustrates a schematic diagram of a patient ventilation system.

Referring to FIG. 1, depicted is a schematic diagram of a patient ventilation system, according to a specific example embodiment of the present disclosure. A patient 102 has a stoma 114 (opening) leading to his/her trachea 116 in which an outer cannula 104 is inserted. The outer cannula 104 may have a curved portion 105, e.g., L shape. A neck flange 106 may be attached to the patient's 102 neck, e.g., by tape and/or straps, etc. (not shown). A ventilator hose 108 may couple a ventilator 110 to a hose coupling 118. Optionally, an inflation collar 112 may be proximate to the outer wall of the outer cannula 104, and an inflation lumen 120 may be within the wall of the outer cannula 104 or proximate thereto. An air valve port 122 may be used in combination with the inflation lumen 120 and the inflation collar 112 for, when inflated, creating an air and/or liquid sealing function between the outer cannula 104 and the trachea 116 air passage. The inflation collar 112 may also position the outer cannula 104 in the trachea 116. More than one lumen may be in the wall of the cannula 104 and the additional lumens therein may be used for various other purposes. The inflation collar 112 may be inflated with a fluid, e.g., air, nitrogen, saline, water, etc.

Figure 2:
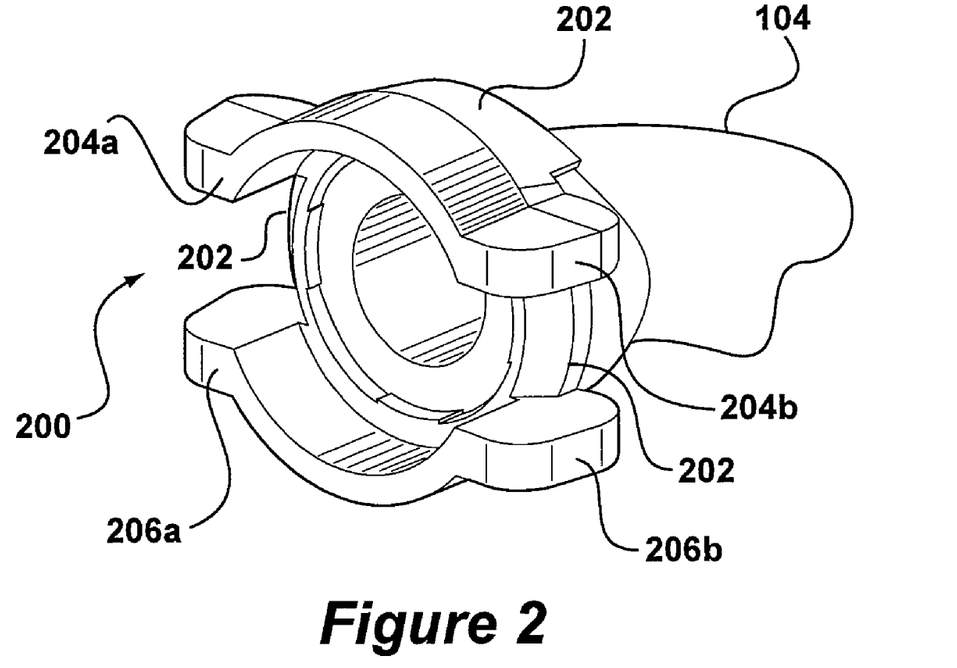
FIG. 2 illustrates a schematic diagram of an outer cannual connector comprising a locking flange having opposing support ears, according to a specific example embodiment of the present disclosure.

Referring to FIG. 2, depicted is a schematic diagram of an outer cannual connector comprising a locking flange having opposing support ears, according to a specific example embodiment of the present disclosure. An outer cannula connector, generally represented by the numeral 200, comprises an outer cannula locking flange 202, a first set of support ears 204a and 204b and a second set of support ears 206a and 206b. The outer cannula connector may be coupled to a proximal end of the outer cannula 104. The second set of support ears 206 are opposite to the first set of support ears 204, e.g., the first and second sets of support ears 204 and 206, respectively, are on opposing sides of each other. Shown are opposing pairs of support ears, however, a single first support ear 204a and a single second support ear 206a opposing the single first support ear 204a may be utilized in accordance with the teachings of this disclosure. It is also contemplated and within the scope of this disclosure that a plurality of opposing support ears may be utilized.

Figure 3:
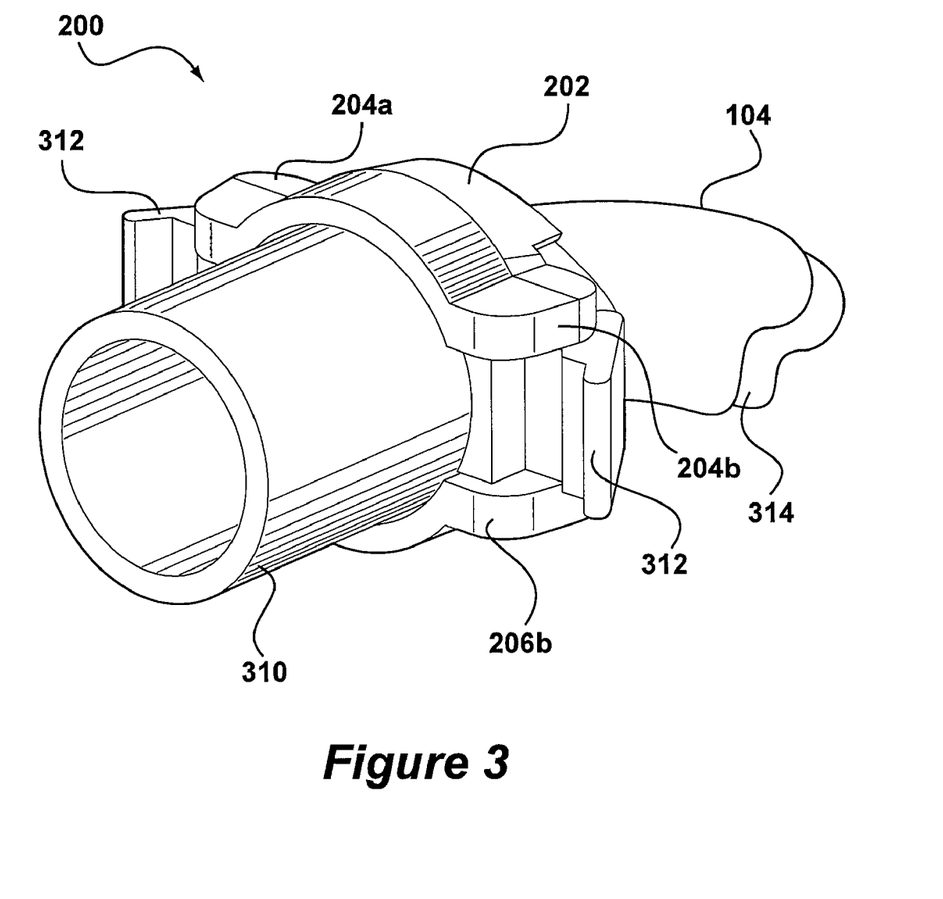
FIG. 3 illustrates a schematic diagram of an inner cannula connector coupled to the outer cannual connector shown in FIG. 2.

Referring to FIG. 3, depicted is a schematic diagram of an inner cannula connector coupled to the outer cannual connector illustrated in FIG. 2. An inner cannula connector 310 has locking ears 312 that may be adapted to engage the outer cannula locking flange 202. The inner cannula 314 may be inserted into an opening (not shown) in the outer cannula connector 200. Inner cannula connector 310 may be coupled to a proximal end of an inner cannula 314. The inner cannula connector 310 may be adapted for coupling to the ventilator hose 108 (see FIG. 1). The inner cannula connector 310 may comprise locking ears 312. A portion of the locking ears 312 and a portion of the inner cannula connector 310 may be placed between the first and second sets of opposing support ears 204 and 206, respectively, and the locking ears 312 may hold, e.g., grasp, clutch, snap, clip, etc., onto the outer cannula locking flange 202. The inner cannula connector 310 may be adapted for coupling to a speaking valve (not shown).

The first and second sets of opposing support ears 204 and 206, respectively, may keep the locking ears 312 substantially aligned therewith, thus preventing rotation of the inner cannula connector 310 within the outer cannula connector 200. The first and second sets of opposing support ears 204 and 206, respectively, may also reduce axial misalignment between the outer cannula flange 200 and the inner cannula connector 310, by preventing substantial torsional radial twisting of the inner cannula connector 310 with respect the outer cannula connector 200. The possibility of locking ears 312 undesirably disengaging, e.g., unlocking, from flange 202 because of rotational and/or radial twisting of the inner cannula connector 310 may be substantially reduced. The inner cannula connector 310 may be, for example but not limited to, an industry standard inner cannula connector 310 having locking ears 312 that are adapted to lock over, e.g., snap over, the flange 202 (FIG. 2) of a mating outer cannula connector 200. The inner cannula 314 and associated connector 310 may be disposable or reusable. The outer cannula 104 and associated connector 200 may be disposable or reusable.

Figure 4:
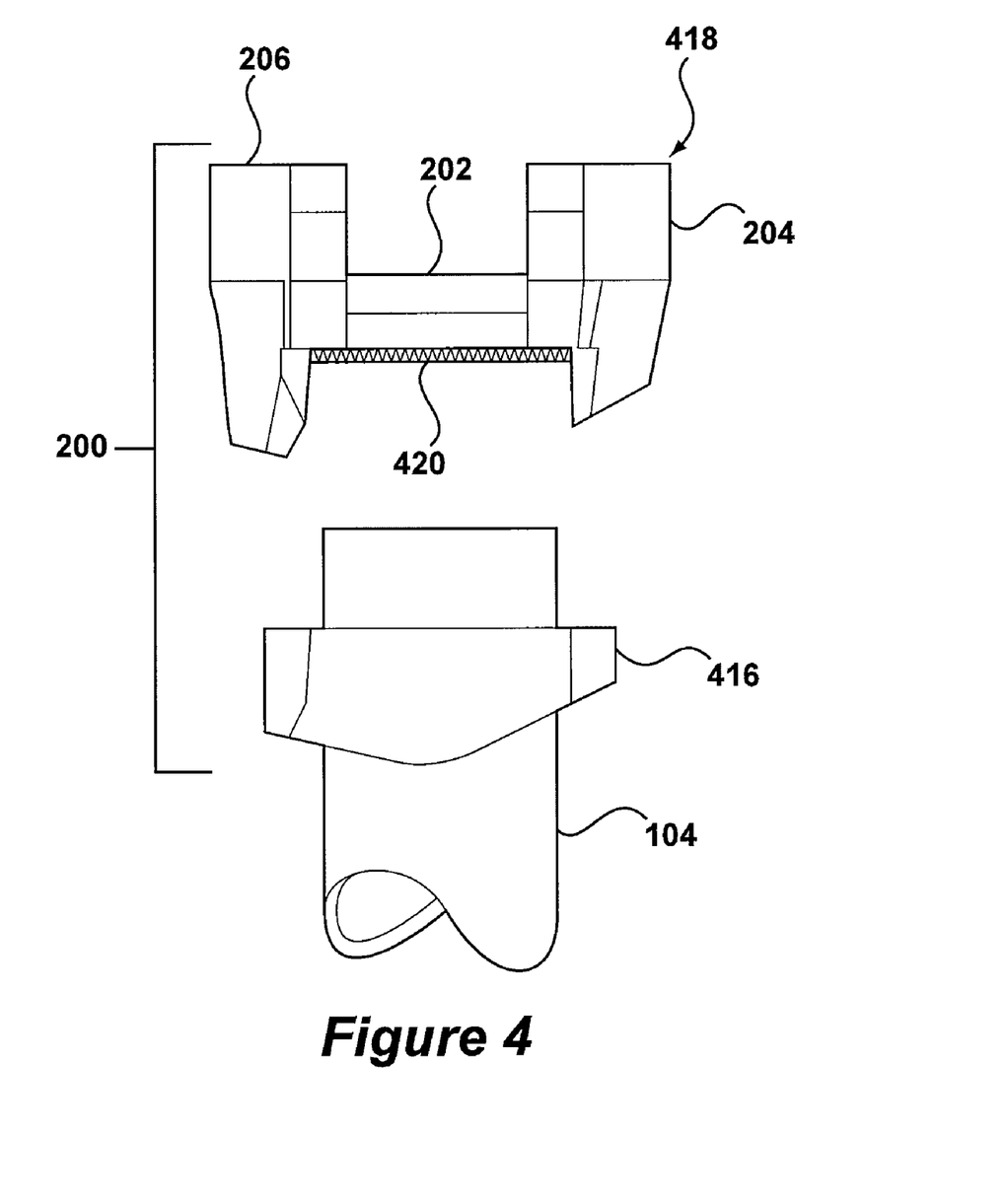
FIG. 4 illustrates an exploded assembly view schematic diagram of the outer cannula connector shown in FIG. 2.

Referring to FIG. 4, depicted is an exploded assembly view schematic diagram of the outer cannula connector 200 shown in FIG. 2. The outer cannula connector 200 may be comprised of a snap-flange hood 418 and a cannula coupling connector 416. The cannula coupling connector 416 may be attached to a proximal end of the outer cannula 104. The snap-flange hood 418 may be comprised of opposing support ears, e.g., the first and second sets of opposing support ears 204 and 206, respectively, and the flange 202.

The snap-flange hood 418 and cannula coupling connector 416 may be attached together by, for example but not limited to, adhesive bonding, ultrasonic bonding, heat staking, solvent bonding; mechanical snaps, threads and pins, etc. Energy directors 420 may be used when the material used for the extended snap-flange hood 418 and coupling flange 416 are ultrasonically welded or heat staked together. The energy directors 420 may be eliminated when the assembly methods used, e.g., solvent bonding, adhesive bonding, or heat staking, spin welding, mechanical snaps or threads, pins, etc., may fuse the snap-flange hood 418 and cannula coupling connector 416 together. Materials that may be used for the cannula coupling connector 416 and snap-flange hood 418 may be, for example but not limited to, polyvinyl chloride (PVC), polycarbonate, ABS, polystyrene, or other plastic material, metal, carbon fiber, etc.

Figure 5:
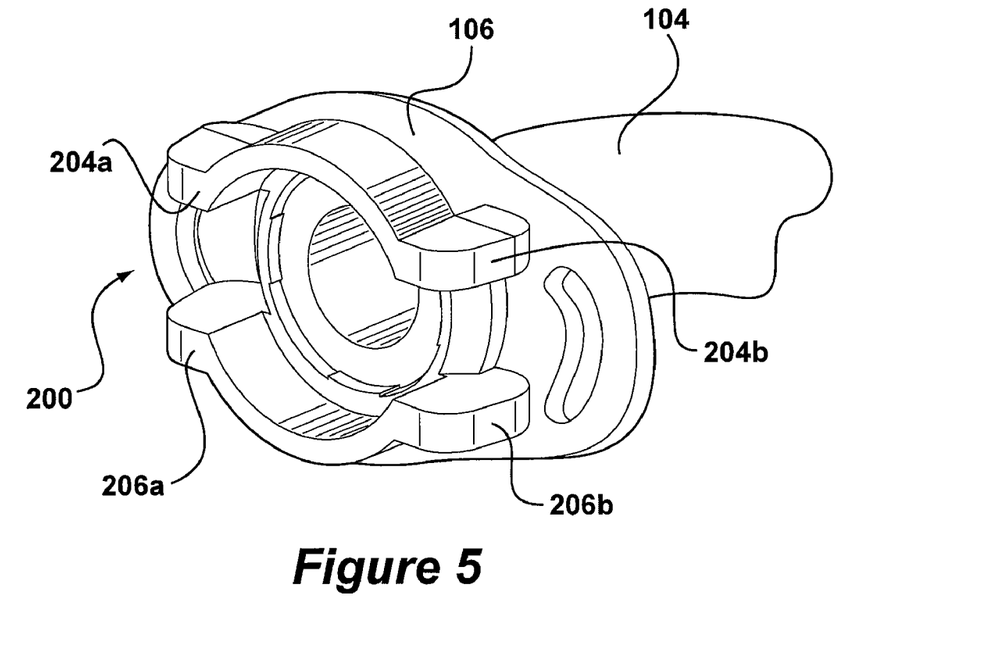
FIG. 5 illustrates a schematic diagram of an outer cannula connector without an inner cannula inserted.

Referring to FIG. 5, depicted is a schematic diagram of an outer cannula connector without an inner cannula inserted.

The neck flange 106 may be positioned in, e.g., snapped onto, the outer cannula connector 200.

Figure 6:
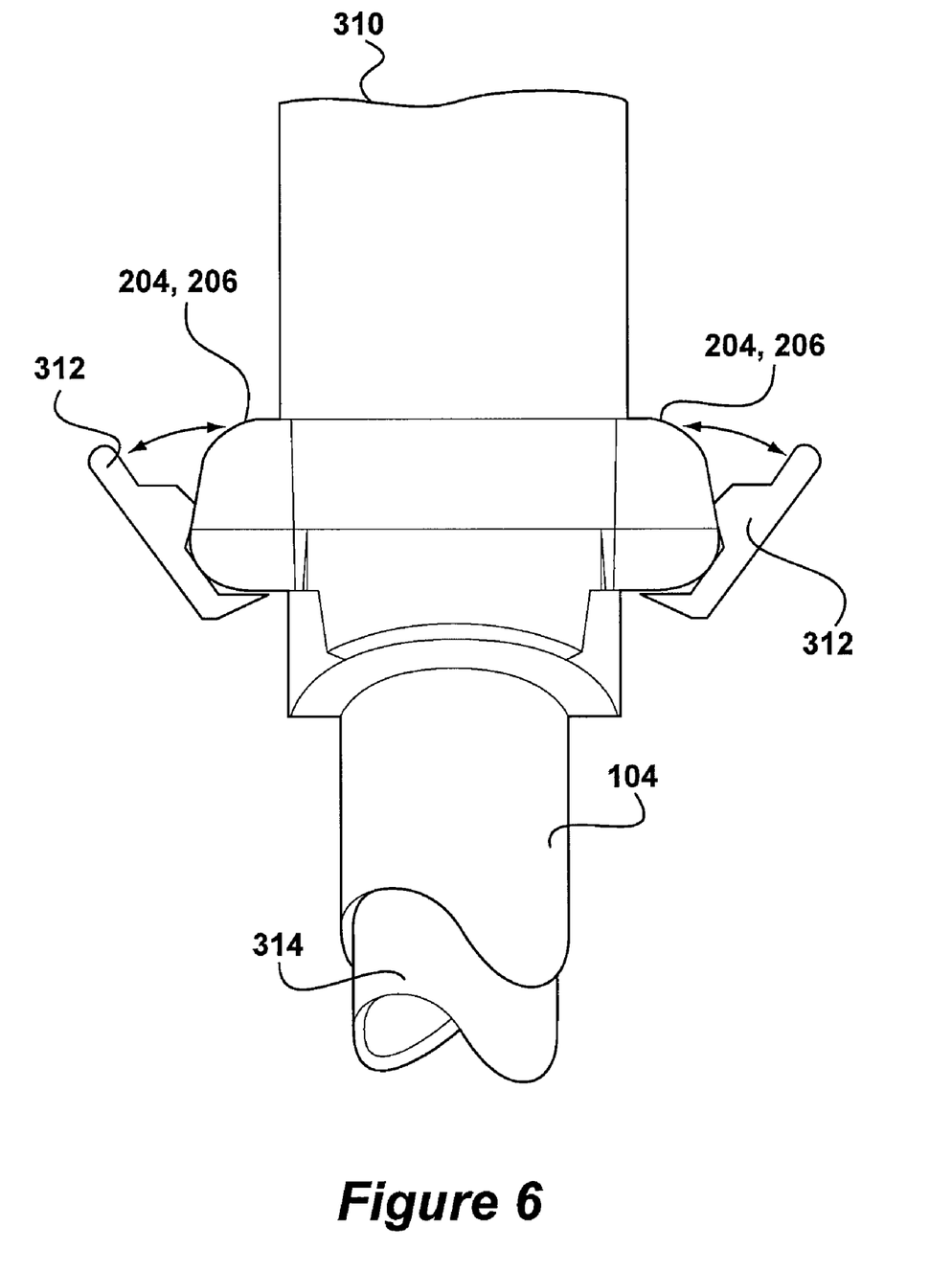
FIG. 6 illustrates a schematic diagram of an inner cannula connector having locking ears supported by opposing sets of support ears of the outer cannula connector, according to a specific example embodiment of the present disclosure.

Referring to FIG. 6, depicted is a schematic diagram of an inner cannula connector having locking ears supported by opposing sets of support ears of the outer cannula connector, according to a specific example embodiment of the present disclosure. In this specific example embodiment, the inner cannula locking ears 312 fasten or connect with, e.g., snap, over flanges 202 (see FIGS. 2 and 3) that are between the first and second sets of support ears 204 and 206, respectively. Placing the locking ears 312 of the inner cannula connector 310 between the first and second sets of opposing support ears 204 and 206, respectively, substantially prevents the locking ears 312 from undesirably disengaging, e.g., unlocking, from the flanges 202, for example, because of twisting and/or radial torque on the inner cannula connector 310.

Figure 7:
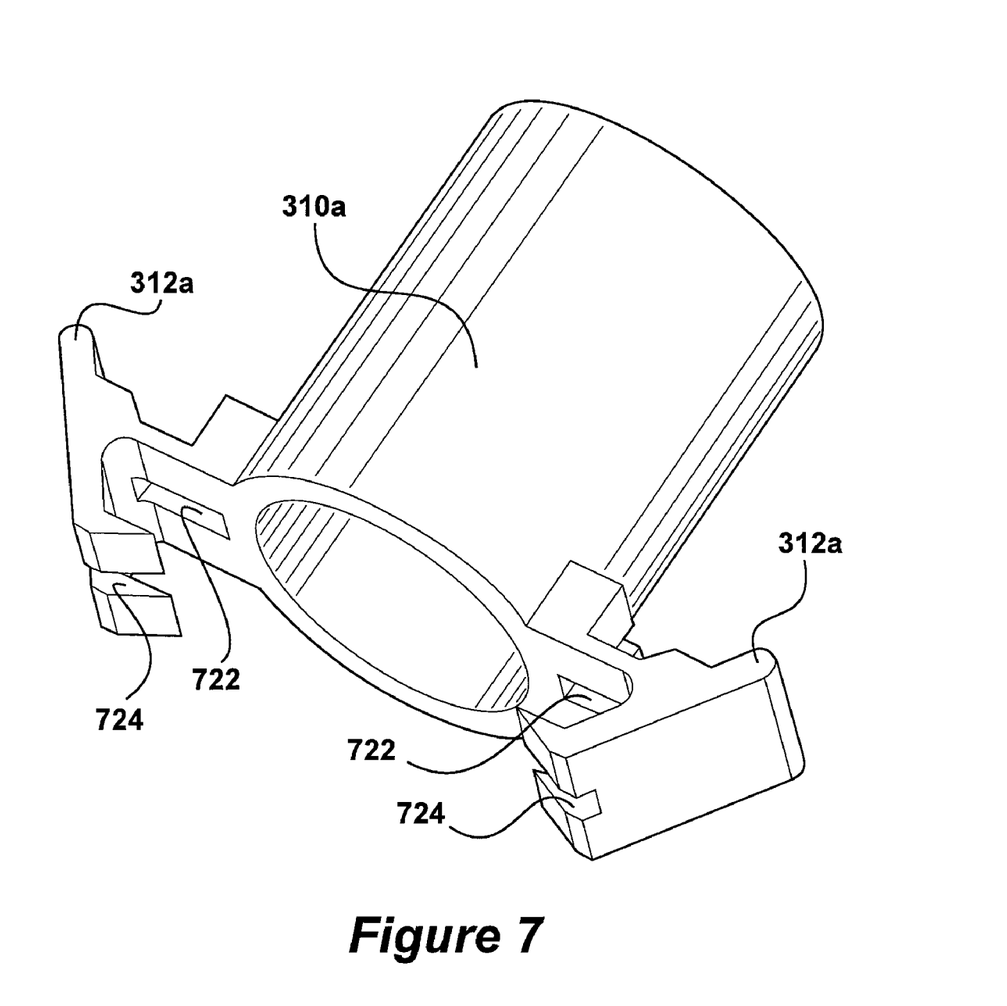
FIG. 7 illustrates a schematic diagram of an inner cannula connector having locking ears with slots adapted for receiving opposing support ears of an outer cannula connector, according to another specific example embodiment of the present disclosure.
Figure 8:
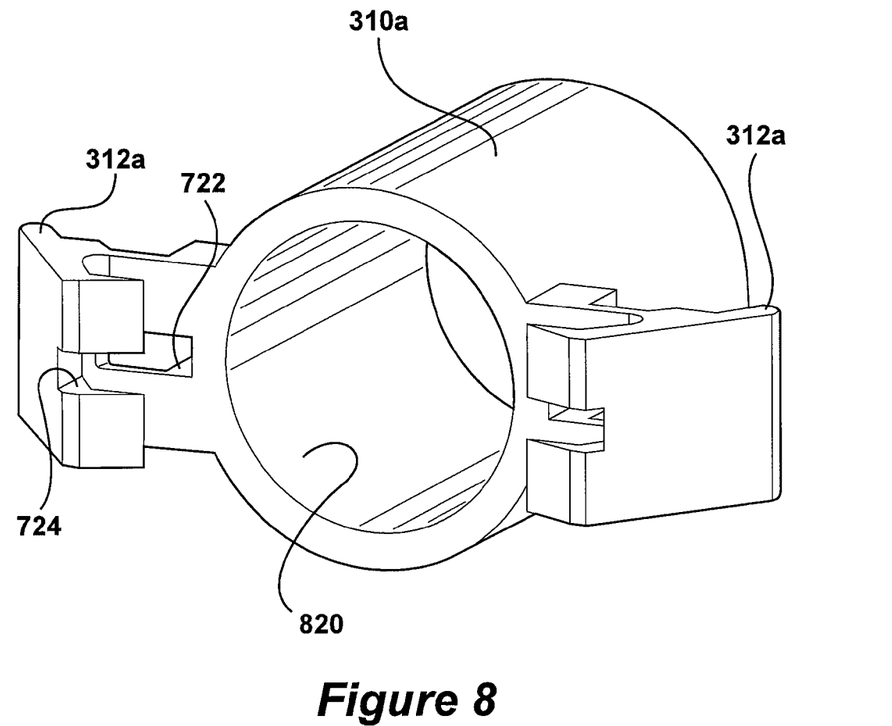
FIG. 8 illustrates a schematic diagram of the inner cannula connector shown in FIG. 6.
Figure 9:
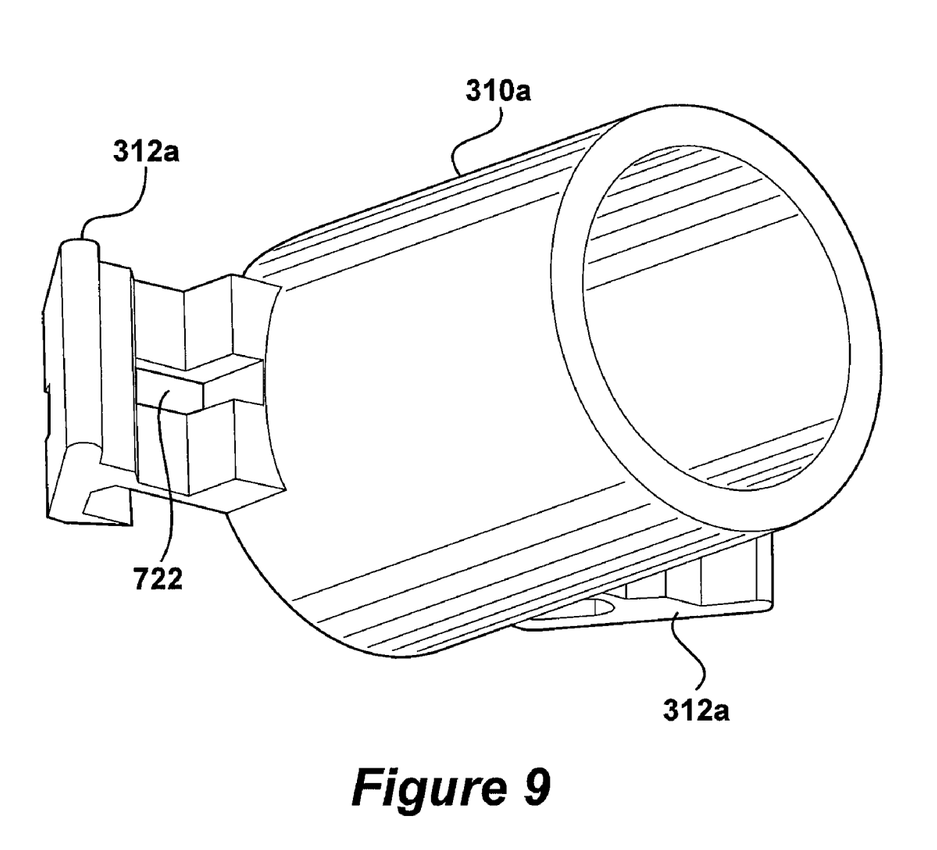
FIG. 9 illustrates a schematic diagram of an opposite view of the inner cannula connector shown in FIG. 6.

Referring now to FIGS. 7-9, depicted are schematic diagrams of an inner cannula connector having locking ears with slots adapted for receiving opposing support ears of an outer cannula connector, according to another specific example embodiment of the present disclosure. An inner cannula connector 310a has locking ears 312a that may be adapted to engage an outer cannula locking flange (e.g., locking flange 202 or locking flange 1012 shown in FIGS. 10-14). The inner cannula connector 310a is attached to a proximal end of an inner cannula and the inner cannula may be inserted into an outer cannula connector (e.g., connector 200 or connector 1000 of FIG. 10). The inner cannula connector 310a may be adapted for coupling to the ventilator hose 108 (see FIG. 1). The locking ears 312a may hold, e.g., grasp, clutch, snap, clip, etc., onto the outer cannula locking flange 202 or locking flange 1012. When placed onto the outer cannula locking flange 202, a portion of the locking ears 312a and a portion of the inner cannula connector 310a may be placed between the first and second sets of opposing support ears 204 and 206, respectively. When placed onto the outer cannula locking flange 1012 shown in FIGS. 10-14, slots 722 and 724 may receive opposing support ears 1014 as shown in FIGS. 10-14. Thus, the inner cannula connector 310a may be used with either the outer cannula connector 200 described hereinabove, or an outer cannula connector 1000 described hereinafter.

Figure 10:
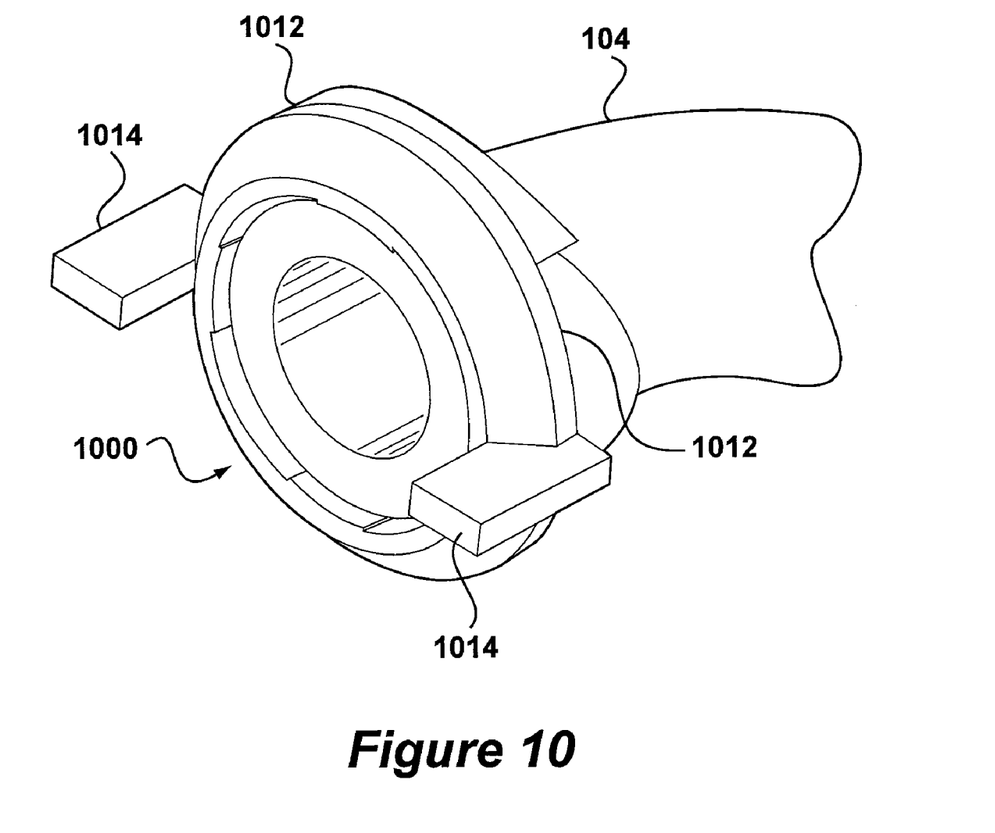
FIG. 10 illustrates a schematic diagram of an outer cannula connector comprising a locking flange having opposing support ears, according to the another specific example embodiment of the present disclosure.
Figure 11:
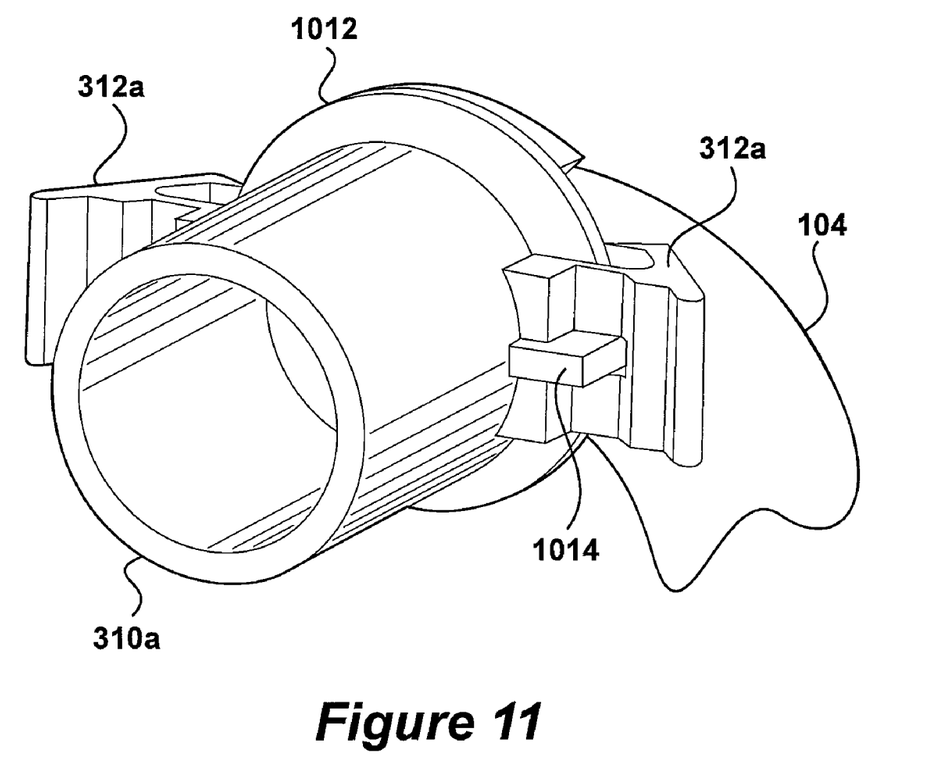
FIG. 11 illustrates a schematic diagram of the outer cannula connector shown in FIG. 10 and inner cannula connector shown in FIGS. 7-9 coupled together.

Referring now to FIG. 10, depicted is schematic diagram of an outer cannula connector comprising a locking flange having opposing support ears, according to the another specific example embodiment of the present disclosure. An outer cannula connector, generally represented by the numeral 1000, comprises an outer cannula locking flange 1012 and opposing support ears 1014, e.g., tabs, prongs, pins, etc. The outer cannula connector 1014 may be coupled to a proximal end of the outer cannula 104.

Figure 12:
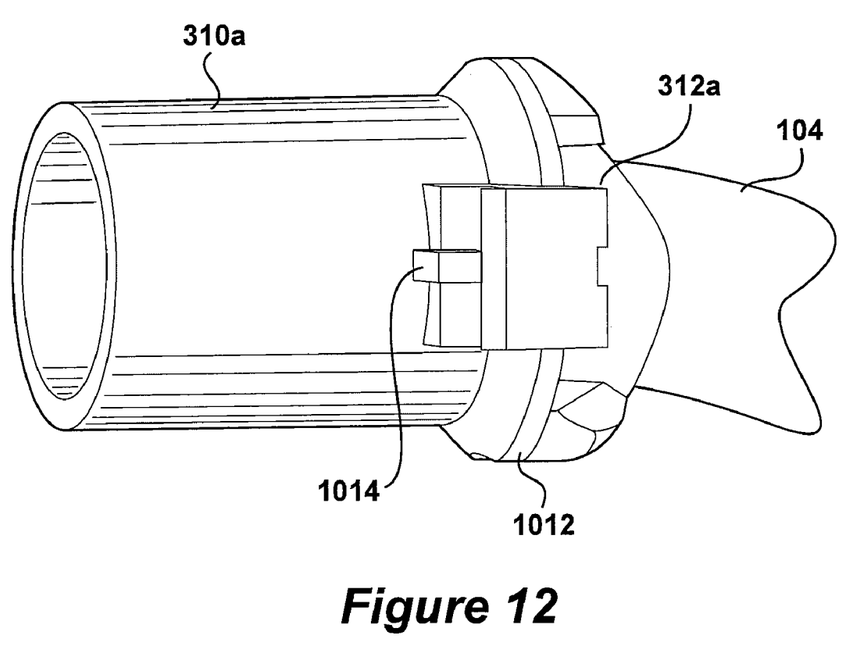
FIG. 12 illustrates a schematic side view diagram of the outer and inner cannula connectors shown in FIG. 10.
Figure 13:
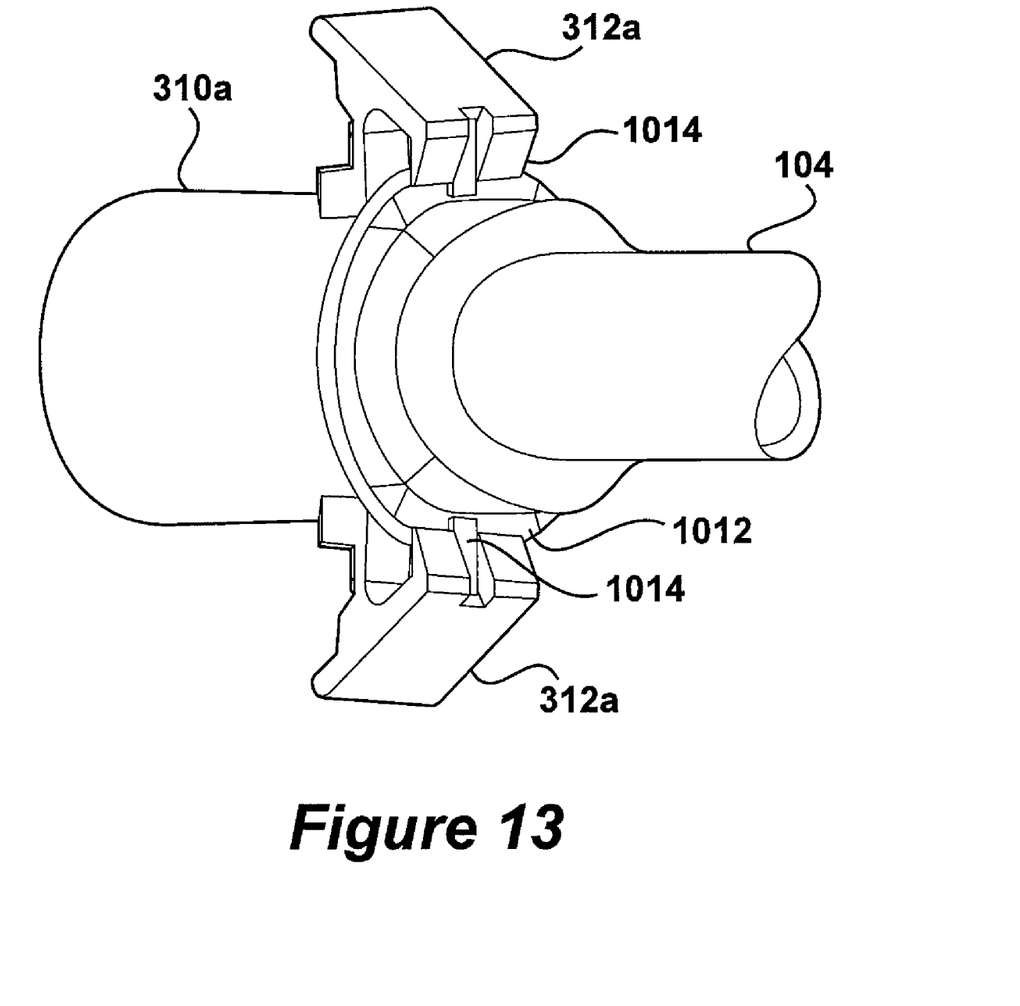
FIG. 13 illustrates another schematic diagram side view of the outer and inner cannula connectors shown in FIG. 10.
Figure 14:
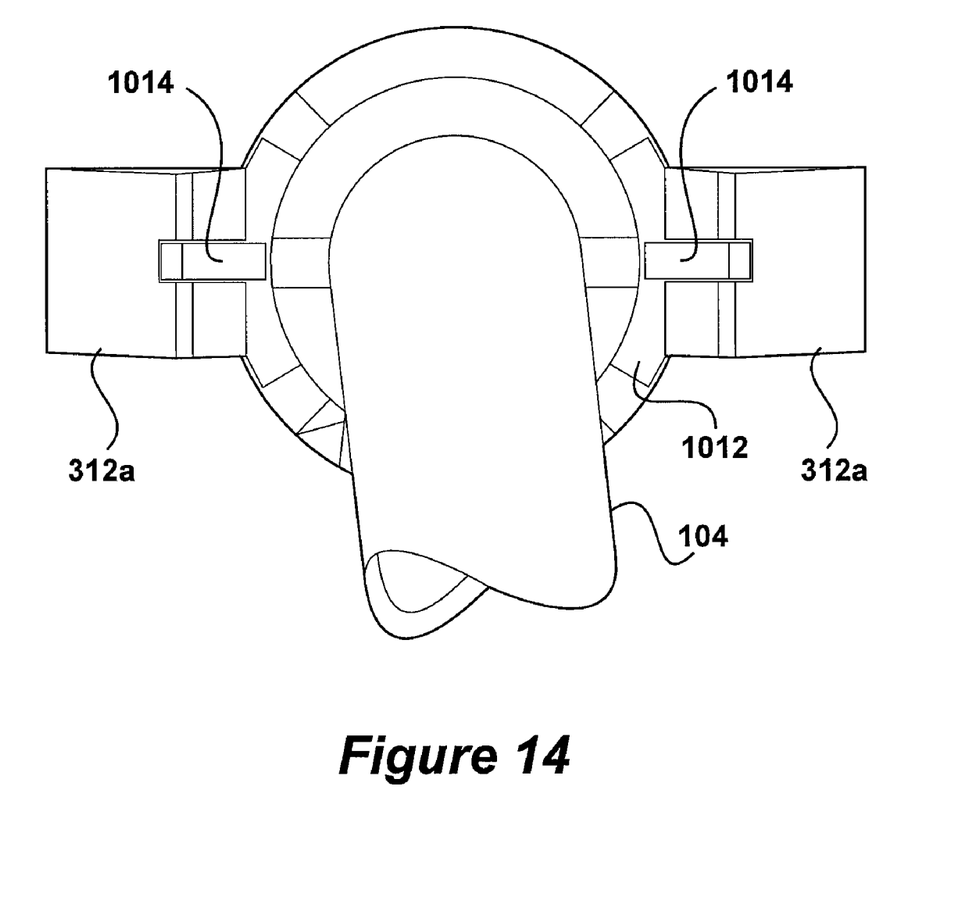
FIG. 14 illustrates a schematic diagram back view of the outer cannula connector shown in FIG. 10 with the inner cannula locking ears engaging the locking flange of the outer cannula connector.

Referring now to FIGS. 11-14, depicted are schematic diagrams at various views of the outer cannula connector shown in FIG. 10 and inner cannula connector shown in FIGS. 7-9 coupled together. The opposing support ears 1014 may slidingly engage into the slots 722 and 724 (FIGS. 7-9) in the locking ears 312a of the inner cannula connector 310a. The opposing support ears 1014 may substantially prevent the locking ears 312a from twisting off of the locking flange 1012 due to, for example, twisting and/or radial torque on the inner cannula connector 310a. FIG. 12 illustrates a schematic side view diagram of the outer and inner cannula connectors shown in FIG. 10. FIG. 13 illustrates another schematic diagram side view of the outer and inner cannula connectors shown in FIG. 10. FIG. 14 illustrates a schematic diagram back view of the outer cannula connector shown in FIG. 10 with the inner cannula locking ears engaging the locking flange of the outer cannula connector.

Specific example embodiments, according to this disclosure may restrict axial rotation from a centered position for example, but not limited to, at a minimum of about +/−0.5 degrees, as much as +/−2 degrees, and possibly as much as +/−10 degrees rotation. Specific example embodiments, according to this disclosure may restrict longitudinal movement for example, but not limited to, at a minimum of about +/−0.005 inches, as much as +/−0.010 inches, and possibly as much as +/−0.10 inches without substantial disengagement.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A method, comprising:
   inserting an inner cannula into an outer cannula, the outer cannula comprising an outer cannula connector having a locking flange and opposing support ears; and
   engaging locking ears of an inner cannula connector associated with the inner cannula such that the locking ears hold onto the locking flange of the outer cannula connector and wherein the opposing support ears extend through structures formed in the locking ears so as to substantially prevent undesired movement of the inner cannula connector in relation to the outer cannula connector.

2. The method according to claim 1, wherein engaging the locking ears with the outer cannula connector prevents the locking ears from rotating axially.

3. The method according to claim 1, wherein engaging the locking ears with the outer cannula connector comprises snapping the locking ears over an edge of the locking flange.

4. The method according to claim 1, wherein engaging the locking ears with the outer cannula connector comprises inserting the locking ears between first and second sets of the opposing support ears.

5. The method according to claim 1, wherein engaging the locking ears with the outer cannula connector comprises inserting the opposing support ears into respective slots in the locking ears adapted to receive the opposing support ears.

6. The method according to claim 5, wherein inserting the opposing support ears into respective slots in the locking ears comprises slidingly engaging the slots with the opposing support ears.

7. The method according to claim 1, wherein engaging the locking ears with the outer cannula connector comprises engaging opposing support ears comprising tabs.

8. The method according to claim 1, wherein engaging the locking ears with the outer cannula connector comprises engaging opposing support ears comprising prongs.

9. The method according to claim 1, wherein engaging the locking ears with the outer cannula connector comprises engaging opposing support ears comprising pins.

10. The method according to claim 1, comprising:
    inflating an inflation collar positioned on an outside surface of the outer cannula with an inflation lumen adapted for directing a fluid to the inflation collar.

11. The method according to claim 1, comprising:
coupling a ventilator hose to the inner cannula connector.

12. A method, comprising:
inserting an inner cannula into an outer cannula, the outer cannula comprising an outer cannula connector having a locking flange and opposing support ears;
engaging locking ears of an inner cannula connector associated with the inner cannula such that the locking ears hold onto the locking flange of the outer cannula connector such that the opposing support ears extend through structures formed in the locking ears; and
inflating an inflation collar with an inflation lumen wherein the inflation collar is positioned on an outside surface of the outer cannula and the inflation lumen is adapted for directing a fluid to the inflation collar for inflation thereof.

13. The method according to claim 12, wherein engaging the locking ears with the outer cannula connector prevents the locking ears from rotating axially.

14. The method according to claim 12, wherein engaging the locking ears with the outer cannula connector comprises snapping the locking ears over an edge of the locking flange.

15. The method according to claim 12, wherein engaging the locking ears with the outer cannula connector comprises inserting the locking ears between first and second sets of the opposing support ears.

16. A method of providing a tracheostomy tube outer cannula connector comprising:
providing a locking flange; and
providing opposing support ears, wherein the opposing support ears are adapted to engage locking ears of an inner cannula connector such that the opposing support ears extend through structures formed in the locking ears so as to substantially prevent undesired movement of the inner cannula connector in relation to the outer cannula connector when engaged.

17. The method of providing a tracheostomy tube outer cannula connector according to claim 16, wherein the locking ears snap over an edge of the locking flange.

18. The method of providing a tracheostomy tube outer cannula connector according to claim 16, wherein the locking ears of the inner cannula connector are adapted to snap onto the locking flange.

19. The method of providing a tracheostomy tube outer cannula connector according to claim 16, wherein the opposing support ears comprise tabs, pins, or prongs.

20. The method of providing a tracheostomy tube outer cannula connector according to claim 16, comprising a snap-flange hood and a cannula coupling connector.

* * * * *